US00PP23647P3

(12) United States Plant Patent
Egger et al.

(10) Patent No.: US PP23,647 P3
(45) Date of Patent: May 28, 2013

(54) ***HEUCHERELLA* PLANT NAMED 'SOLAR ECLIPSE'**

(50) Latin Name: ***Heucherella* hybrid**
Varietal Denomination: Solar Eclipse

(75) Inventors: Janet N. Egger, Wilsonville, OR (US); John C. Pavlich, East Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 82 days.

(21) Appl. No.: 13/200,474

(22) Filed: Sep. 22, 2011

(65) Prior Publication Data

US 2013/0081184 P1 Mar. 28, 2013

(51) Int. Cl.
*A01H 5/00* (2006.01)

(52) U.S. Cl.
USPC ..... Plt./441

(58) Field of Classification Search ..... Plt./441
See application file for complete search history.

*Primary Examiner* — June Hwu
(74) *Attorney, Agent, or Firm* — Klarquist Sparkman, LLP

(57) ABSTRACT

A new and distinct *Heucherella* plant substantially as shown and described, characterized by large red to brown leaves with a yellow to lime margin, leaves which are palmately lobed, scalloped, and slightly ruffled, a high crown count, a tight, mounding plant habit, and excellent vigor. It grows equally well in full sun or filtered shade in the Pacific Northwest.

1 Drawing Sheet

Botanical denomination: *Heucherella* hybrid.
Variety designation: 'Solar Eclipse'.
Cross reference to *Heucherella* 'Solar Power' U.S. Plant Pat. No. 22,427

BACKGROUND OF THE INVENTION

The present invention relates to a new and distinct cultivar of *Heucherella* and given the cultivar name of 'Solar Eclipse'. *Heucherella* is in the family Saxifragaceae. *Heucherella* 'Solar Eclipse' originated from a tissue culture mutation from *Heucherella* 'Solar Power Eclipse'.

SUMMARY OF THE INVENTION

Compared to the mother plant *Heucherella* 'Solar Power', the new cultivar has a higher crown count, a tighter mounding habit, more rounded leaf lobes, a more ruffled leaf margin, and a much darker leaf center pattern which encompasses the whole leaf except the edge.

Compared to *Heucherella* 'Sonic Smash', U.S. Plant Patent applied for, the new cultivar has a denser crown, shorter flower stems, a broader and permanent dark pattern on the leaves, and yellow rather than green spring leaves.

This new *Heucherella* is uniquely distinguished by:

1. large red to brown leaves with a yellow to lime margin,
2. palmately lobed leaves which are scalloped, slightly ruffled,
3. a high crown count,
4. a tight, mounding plant habit,
5. grows equally well in full sun or filtered shade in the Pacific Northwest, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a nine-month-old *Heucherella* 'Solar Eclipse', growing in a one gallon container in a cool greenhouse in May in Canby, Oreg.

FIG. 2 shows the foliage color of a one and a half year old *Heucherella* 'Solar Eclipse' grown in the shade in late summer in Canby, Oreg.

DETAILED PLANT DESCRIPTION

The following is a detailed description of the new *Heucherella* cultivar based on observations of a one and a half-year-old specimen growing in a 2 gallon container in a cool greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Basal rosette, herbaceous perennial.
*Hardiness*.—USDA Zone 4 to 9.
*Size*.—20 cm tall from top of the foliage to the ground and 50 cm wide.
*Habit*.—Mounding.
*Vigor*.—Excellent.
*Roots*.—Fibrous, freely branching, fine, and white in color.

Leaf:

*Type*.—Simple.

*Arrangement*.—Rosette.

*Shape*.—Ovate.

*Lobing/division*.—7 palmate rounded lobes with the terminal the longest, the terminal lobe with shallow secondary lobes.

*Venation*.—Palmate, color topside Yellow Green N144C, bottom side Yellow Green 146A.

*Margins*.—Crenate, slightly undulate.

*Apex*.—Mucronulate.

*Base*.—Cordate, overlapping at the base.

*Blade size*.—Grows to 10 cm long and 9 cm wide.

*Surface texture*.—Glandular both surfaces.

*Petiole description*.—Grows to 18 cm long and 3 mm wide, glandular hairs, color between Greyed Purple 183D and 186D on bottom half and lightening to between Yellow Green 148C and 152D.

*Leaf color*.—New leaves in spring and fall topside Greyed Purple 187A with leaf margin Yellow Green N144C; bottom side closest to Brown N200B with the margin Yellow Green 146A; summer, winter mature leaves topside Greyed Purple N187A with the margin Yellow Green 146B, bottom side Brown N200B with the margin Yellow Green 146A.

Inflorescence:

*Size*.—5 cm wide and 12 cm long.

*Type*.—Raceme.

*Number of flowers per raceme*.—About 70.

*Number of racemes*.—About 35 in first spring flush.

*Peduncle*.—Grows to about 44 cm tall, 3 mm wide at base, Yellow Green 146C, glandular hairs, with 0-2 branches with cauline leaves at the base (cauline leaves petiolate, blades 4 cm long and 3.5 cm wide, ovate, sometimes palmately lobed, margins broadly crenate, Yellow Green N144C with leaf center irregularly splattered Greyed Purple 187A).

*Pedicel*.—Grows to 12 mm long, with glandular hairs, Greyed Red 182B.

*Bloom period*.—April to July in Canby, Oreg.

Flower bud:

*Size*.—1.5 mm wide and 3 mm long.

*Description*.—Glandular puberulent, ovoid.

*Color*.—NN155A.

Flower:

*Type*.—Perfect.

*Shape*.—Campanulate.

*Size*.—5 mm deep and 7 mm wide.

*Petal description*.—5 in number, oblanceolate, 35 mm long and 1 mm wide, tip acuminate, base attenuate, margin entire, glabrous on both sides, White NN155D on both sides.

*Calyx description*.—3 mm deep and 5 mm wide, with 5 lobes, divided ½ way to the base, campanulate, glandular hairs on outside, glabrous inside, tip obtuse, margin entire, White NN155C on both sides.

*Stamen description*.—5 in numbers, filaments 3 mm long, White NN155D, anthers sterile, less than 1 mm, Greyed Orange 164A.

*Pistil description*.—One central two beaked pistil, 4 mm long, White 155B.

*Fragrance*.—None.

*Lastingness*.—Each raceme blooms for about 2 weeks on the plant.

Fruit and seed: None.

Disease and pest tolerance: No known resistances. Excellent disease tolerance to powdery mildew. All *Heucherella* are susceptible to root weevils.

We claim:

1. A new and distinct *Heucherella* plant as herein illustrated and described.

* * * * *

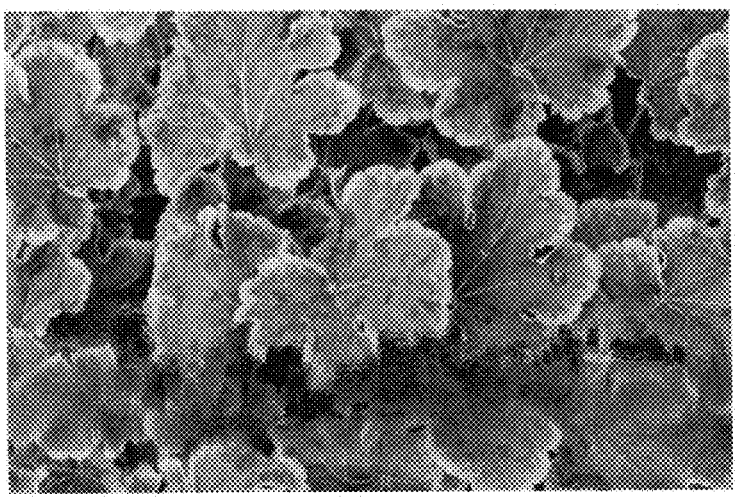

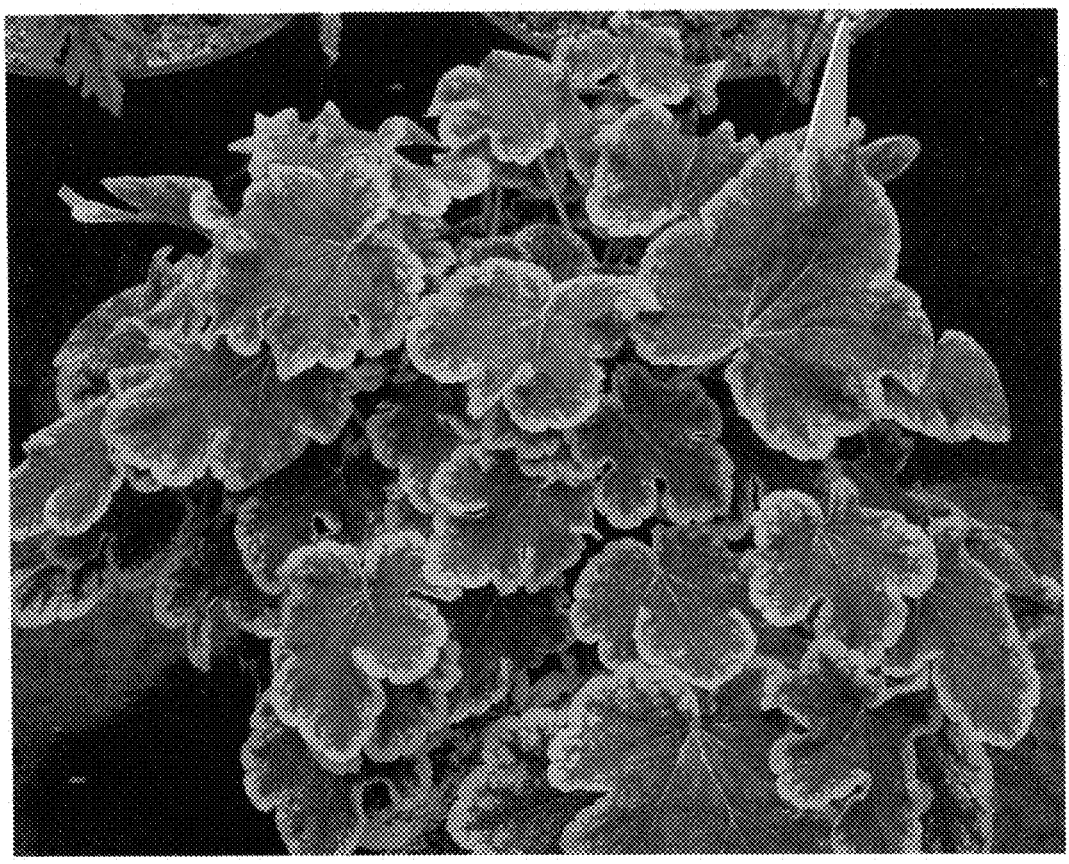
FIG. 1 above, FIG. 2 below